(12) United States Patent
Walter et al.

(10) Patent No.: US 9,144,481 B2
(45) Date of Patent: Sep. 29, 2015

(54) PACKAGE FOR A DENTAL MATERIAL AND A METHOD OF MANUFACTURING THE PACKAGE

(75) Inventors: Alexander Walter, Pürgen (DE); Marc Peuker, Schondorf (DE); Michael Sogl, Seefeld (DE); Dieter Poschmann, Starnberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 73 days.

(21) Appl. No.: 13/812,307

(22) PCT Filed: Jul. 25, 2011

(86) PCT No.: PCT/US2011/045185
§ 371 (c)(1),
(2), (4) Date: Jul. 8, 2013

(87) PCT Pub. No.: WO2012/015739
PCT Pub. Date: Feb. 2, 2012

(65) Prior Publication Data
US 2013/0284620 A1 Oct. 31, 2013

(30) Foreign Application Priority Data
Jul. 29, 2010 (EP) .................................. 10171192

(51) Int. Cl.
*A61C 19/00* (2006.01)
*A61C 5/06* (2006.01)
*B65D 81/32* (2006.01)
*B65B 43/00* (2006.01)

(52) U.S. Cl.
CPC ................ *A61C 19/005* (2013.01); *A61C 5/06* (2013.01); *B65B 43/00* (2013.01); *B65D 81/3266* (2013.01)

(58) Field of Classification Search
CPC ........ A46B 11/001; A46B 17/04; A61C 3/05; A61C 5/066; A61C 5/068; A61C 19/005; A61C 19/02; B65D 33/004; B65D 77/245; B65D 81/3266; B65B 43/00
USPC .............. 206/15.2, 15.3, 63.5, 209, 229, 230, 206/361, 438; 222/94, 145.1, 145.5
See application file for complete search history.

(56) References Cited

U.S. PATENT DOCUMENTS

| | | | |
|---|---|---|---|
| 5,009,894 | A | 4/1991 | Hsiao |
| 6,105,761 | A | 8/2000 | Peuker |

(Continued)

FOREIGN PATENT DOCUMENTS

| | | |
|---|---|---|
| DE | 10009629 | 9/2001 |
| EP | 0895943 | 2/1999 |

(Continued)

OTHER PUBLICATIONS

International Search Report for International Application No. PCT/US2011/045185, mailed on Dec. 19, 2011, 5 pages.

*Primary Examiner* — Bryon Gehman

(57) ABSTRACT

A package for a dental material comprises a compartment for holding a first substance of the dental material and an open reservoir at least partially formed by a wall of the package. The package is adapted such that the compartment and the reservoir are connectable for fluid communication. The reservoir accommodates a second substance of the dental material retained at a surface of the reservoir wall. The package preferably enables easy mixing of the dental material from the first and second substance, thus preferably facilitate a preparation and use of the dental material.

16 Claims, 5 Drawing Sheets

(56) References Cited

U.S. PATENT DOCUMENTS

| | | | |
|---|---|---|---|
| 7,048,911 B2 * | 5/2006 | Cashman et al. | 206/63.5 |
| 7,097,075 B2 * | 8/2006 | Peuker et al. | 206/221 |
| 7,320,398 B2 * | 1/2008 | Bertl et al. | 206/229 |
| 7,374,040 B2 * | 5/2008 | Lee et al. | 206/229 |
| 2003/0038040 A1 | 2/2003 | Bertl | |
| 2003/0225354 A1 | 12/2003 | Drake | |
| 2011/0027750 A1 * | 2/2011 | Boehm et al. | 433/89 |

FOREIGN PATENT DOCUMENTS

| | | |
|---|---|---|
| WO | WO 88-06558 | 9/1988 |
| WO | WO 97-23190 | 7/1997 |
| WO | WO 01-64547 | 9/2001 |
| WO | WO 2008-134466 | 11/2008 |
| WO | WO 2008-157795 | 12/2008 |
| WO | WO 2009-085636 | 7/2009 |

\* cited by examiner

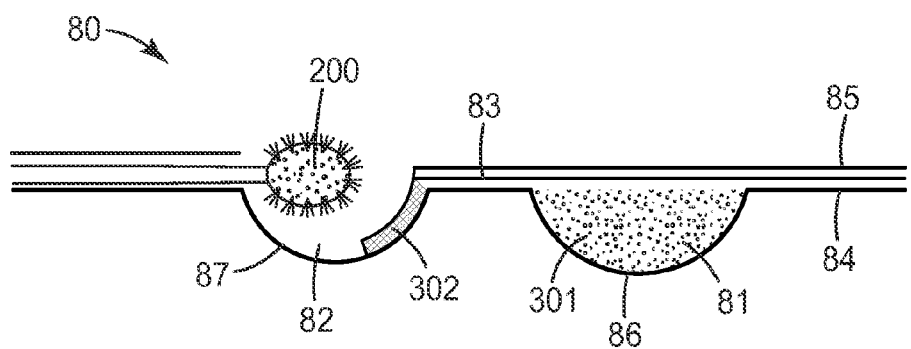
FIG. 8
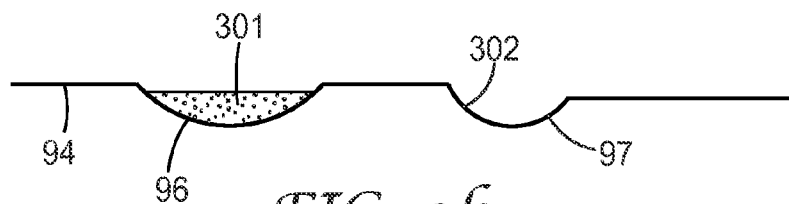
FIG. 9a
FIG. 9b
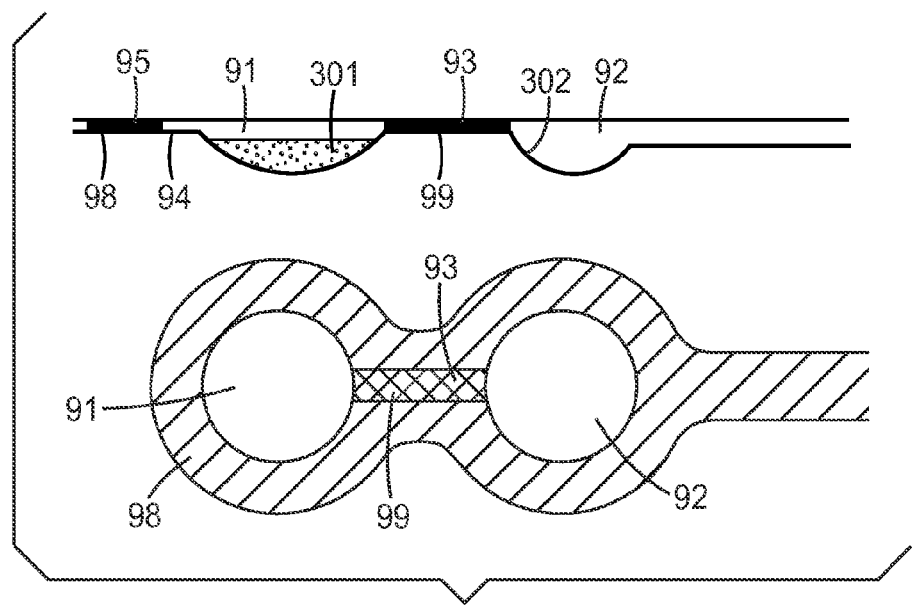
FIG. 9c

PACKAGE FOR A DENTAL MATERIAL AND A METHOD OF MANUFACTURING THE PACKAGE

CROSS REFERENCE TO RELATED APPLICATIONS

This application is a national stage filing under 35 U.S.C. 371 of PCT/US2011/045185, filed Jul. 25, 2011, which claims priority to European Application No. 10171192.7, filed on Jul. 29, 2010, the disclosures of which are incorporated herein by reference in their entirety.

FIELD OF THE INVENTION

The invention relates to a package for a dental material, and in particular to a package comprising a compartment for holding a first substance of the dental material and an open reservoir accommodating a second substance of the dental material retained in the open reservoir. Further the invention relates to a method of manufacturing such a package.

BACKGROUND ART

In the dental field a number of liquid and semi-liquid compositions are made from two or more flowable components that are typically separately stored, and only mixed together immediately prior to use. For example, certain dental compositions like dental adhesives, sealants or etchants are offered in packages that initially store components of the dental composition separate from one another. The dental compositions then can be obtained by mixing the components at the time, and in the amount needed. After mixing the components, the dental composition may be applied to a desired place, for example in the cavity of a tooth in a patient's mouth.

A variety of packages have been proposed over the years for separately containing and storing components of multi-component compositions. Examples of packages for multi-component compositions include dual-chamber cartridges, dual-chamber syringes or dual-chamber blister packages. Such packages are typically designed to provide a readily mixable composition, or to provide the components individually for subsequent mixing. There are also single use packages for providing suitable amounts of composition for a single treatment.

For example U.S. Pat. No. 6,105,761 discloses a device for storing and dispensing flowable substances. The device includes a container formed by two sheets that are interconnected by heat sealing. The sheets form a compartment for receiving a component, which may be a liquid, and a pocket for receiving a brush. In the area between the compartment and the pocket, the connection between the sheets includes a pre-defined break zone which can be released by pressure exerted on the compartment, to force the liquid from the compartment into the pocket and to wet the tip of the brush disposed therein.

There is still a desire for packages that can be used to provide multi-component compositions for different applications. In particular, suitable packages for providing relatively small amounts of a composition are desirable. Moreover, there is a need for packages that can be used in health care fields, like dentistry, in which a relatively high level of hygiene is required. There is also a general need for packages that are relatively inexpensive to manufacture and use.

SUMMARY OF THE INVENTION

The invention is directed to a package for a dental material. The package comprises a compartment for holding a first substance of the dental material and an open reservoir. The open reservoir in one aspect of the invention is at least partially formed by a wall of the package. The package is preferably adapted such that the compartment and the reservoir are sealed from each other. Further the package is adapted such that the compartment and the reservoir are connectable for fluid communication. The reservoir accommodates a second substance of the dental material retained at a surface of the reservoir wall.

The invention is advantageous in that it preferably allows a single component package to be used as two- or multiple-component package. For example a package having a single compartment for holding a first substance and a reservoir for receiving the first substance may be used as single-, two- or multiple-component package without substantially modifying the structure of the package. Further the invention may allow for hindering a substance which requires the presence of air during storage from escaping from the package although the substance is stored in an open reservoir of the package. Further the invention may facilitate handling of a material packaged in the package, and thus may help minimizing costs.

In one embodiment the compartment is closed and encapsulates the first substance, whereas the reservoir is open and the second substance is retained therein. Thus the package may be adapted such that the second substance can interact with the outside of the package whereas the package is further adapted to encapsulate the first substance from the outside.

In one embodiment the package forms one piece, meaning that the compartment and the reservoir are mechanically connected. Thus the compartment and the reservoir are jointly provided to a user. Therefore a user may be prevented from combining different reservoirs with different compartments, for example from multiple packages. This may facilitate the use of the package and may provide for a relatively reliable operation of the package. The package may for example be configured for single use. The compartment may for example comprise the first and second substance in predefined amounts providing for an amount of dental material that is sufficient for one use. After use the package may be disposed.

In one embodiment the compartment is formed between interconnected sheet-like layers of the package. The reservoir may be formed by at least one of the sheet-like layers. Therefore at least one of the sheet-like layers further preferably forms the reservoir wall. For example the sheet-like layers each may have a major surface, and the major surfaces may be interconnected. The interconnection may comprise at least one of an adhesive bond, and a welded interconnection.

In another embodiment the package further comprises an openable seal which separates the reservoir and the compartment from each other. The seal is preferably formed by an area in which the layers are interconnected. The interconnection in this area is preferably non-permanent such that forcing the first substance between the layers causes the layers to separate. Thus the seal is preferably adapted to close a passageway between the reservoir and the compartment and to automatically open the passageway upon the first substance being forced toward the seal. The passage may be formed by an interruption of a permanent seal of the layers. Thus the interconnection closing the compartment may be formed by a combination of a permanent and a non-permanent seal, and the non-permanent seal may be openable to open the compartment.

In one embodiment the sheet-like layers together form a sandwich enclosing the first substance between. Further the sheet-like layers may together form a sandwich retaining the second substance between the layers. For example the second substance may be predominantly held in place by a mechanical force exerted by the layers urged toward each other. Therefore additional means for retaining the second substance may be unnecessary.

In a further embodiment the compartment comprises the first substance provided in a flowable mass. The first sustance may form the flowable mass or may be part of it. For example the first substance may be a dental adhesive or a dental flowable composite, or a component thereof. Further the second substance may be provided in a generally non-flowable mass. Again the second substance may form the non-flowable mass or may be part of it. For example the second substance may be a dental adhesive or a dental flowable composite, or a component thereof. The non-flowable mass may further comprise a binder or film former.

In one embodiment the second substance may comprise a film former. A film former can generally be described as a substance which can be provided in a liquid and which may be solidified in such a manner as to form a substantially solid film on the surface. The film former may for example be provided in a solvent, for example water, and the solvent may be substantially removed to make the film former to form a substantially solid or substantially non-flowable film. This may for example be achieved by a drying action in which at least part of the solvent is removed. The film former may provide for retaining the second substance of the dental material at the surface of the reservoir wall in the open reservoir. For example the film former may form a matrix material which embeds the second substance, or the film former and the second substance may be provided as a mixture or blend.

The molecular weight (Mw) of the film former can vary over a wide range (e.g. from about 1000 to about 1,200,000). Typical ranges include from about 10,000 to about 400,000, or from about 20,000 to about 200,000. The film caused or produced by the film former typically has a thickness in a range from about 0.5 μm to about 100 μm or from about 10 μm to about 50 μm.

Film formers or film forming agents can be classified as natural film formers, semi-synthetic film formers, cellulose derivatives, poly(meth)acrylates and vinyl polymers. Particular examples include (for example fully or partially hydrolyzed) polyvinylalcohol, polymethylvinylether, polyvinylpyrrolidone, (for example aqueous) acrylic resin dispersions (for example Eudragit™, commercially available from Rohm), gelatine, polysaccharides (for example agarose), polyacrylamide, copolymers of vinylpyrrolidinone and acrylamide, hydrophilic cellulose derivatives (for example hydroxyethylcellulose, hydroxypropylcellulose, methylcellulose), homo- and copolymers of polyvinylacetate, homo- and copolymers of polyvinylpropionate, styrene acrylics, ethylene vinyl acetate, polyurethanes, hydroxylated acrylates such as poly(hydroxyethyl methacrylate), poly(vinylethylene glycol acrylate), and combinations and mixtures thereof.

In one embodiment the reservoir comprises a cavity which is open toward the reservoir. The second substance may be at least partially accommodated in the cavity. Therefore the reservoir may have an overall reservoir surface having openings into the cavities. Accordingly the first substance may be accommodated in the cavity beneath the overall reservoir surface. Thus at least a part of the first substance may be protected from being stripped off by an item contacting the overall reservoir surface. For example an applicator moved or stored in the reservoir may be hindered in loosening the second substance from the reservoir wall. The cavity may be formed by a bulge in the reservoir wall, for example. Such a cavity or cavities may allow for maximizing the surface area of the reservoir so that which a maximized amount of the second substance can be deposited. This applies also to a roughened of grooved surface area of the reservoir. The capacity of the cavity is preferably smaller than the capacity of the remainder of the reservoir. For example the bulge forming the reservoir may comprise a smaller bulge accommodating the second substance at least partially. The bulge may be shaped such that its opening has a general shape corresponding to at least one of a circle, an oval, and a bar-shape. Different shapes of the opening may provide for different levels of retention of the second substance in the reservoir. The shape may for example be selected such that the second substance is sufficiently retained in the reservoir during storage of the package, and further such that the second substance can easily mix with the first substance when received in the reservoir. The package may further comprise a plurality of similar or differently shaped cavities. Thus the capacity of the cavities as well as storage and mixing properties of the second substance may be optimized as desired. The skilled person will recognize a variety of alternative configurations of the cavities. In one example the cavities are formed by a rough surface having an average surface roughness Ra of between about 10 μm and about 500 μm according to DIN EN ISO 4287 or 4288 respectively.

In one embodiment the reservoir accommodates a third substance. The package may comprise features to accommodate the third substance that are similar and/or equal to the features allowing accommodation of the second substance as described herein. Further the third substance may have general characteristics (for example may be non-flowable) that correspond to characteristics of the second substance. The skilled person will recognize that an accommodation of further substances is likewise possible.

In a further embodiment the second and third substances are positioned substantially separate from one another. The second and third substances may be arranged adjacent or adjoining but may otherwise be separate from one another. Thus components of the second and third substances that may interact with one another may be kept separate until the package is used. This may provide for maximizing a time period over which the package can be stored without the substances substantially altering due to interaction.

In one embodiment the reservoir comprises a coating in which at least a portion of at least one of the second and third substances is accommodated. The reservoir may comprise a coating in which at least a portion of the second substance and at least a portion of the third substance are accommodated. In more particular the reservoir may comprise a coating in which the second substance and the third substance are accommodated. The coating may comprise a first coating area and a second coating area. In the first coating area at least a portion or all of the second substance may be accommodated. Further in the second coating area at least a portion or all of the third substance may be accommodated. Again the coating areas may be arranged adjacent or adjoining.

In a further embodiment the package comprises a first reservoir in which at least a portion of the second substance is accommodated, and a second reservoir in which at least a portion of the third substance is accommodated. Thus the package may have two or more reservoirs. Such a package preferably comprises a first seal which separates the first reservoir and the compartment from one another, and a second seal separating the second reservoir and the compartment from one another. This preferably allows a user of the package to select between a use of the first substance with the second substance or the first substance with the third substance. For example the second and third substances may be generally similar or equal in composition, but present at different amounts in the first and second reservoirs. Therefore the package may be adapted to provide the dental material composed of two or more substances at two or more different mixing ratios. This may for example be used for the preparation of coloring solutions. In this case the same package may be adapted to provide two different colors. The skilled person will recognize further applications, like the preparation of dental material at different viscosities, or dental adhesives which are adapted for adhesion at different materials like for example dentin and enamel, or metal and ceramic. In one example only one of the first and second reservoirs contains the second and/or third substance. Therefore the first substance may be used alone if transferred in one of the reservoirs or in combination with the second and/or third substance if transferred in the other one of the reservoirs.

The package having a first and a second seal may be activated by compressing the compartment at an area of one of the seals and shifting the compression toward the other one of the seals (similar to a compression of a tube starting from the tube crimp toward the tube opening). It has been found that typically the seal toward which the first substance is urged opens while the other seal stays closed. Therefore opening of the desired seal of the package may be reliably controlled by a user.

A further aspect of the invention relates to a package which comprises a compartment for holding a first substance of the dental material and an open reservoir. The package may be formed of at least two separate (not physically connected) partial packages, for example a container which forms the compartment, and a separate well forming the reservoir. The open reservoir according to this aspect of the invention is preferably formed by a wall of one of the partial packages. The package is preferably adapted such that the compartment and the reservoir are sealed from each other. Further the package is adapted such that the compartment and the reservoir are connectable for fluid communication. The reservoir accommodates a second substance of the dental material retained at a surface of the reservoir wall.

The container may comprise the first substance (for example in a flowable mass), and the well may comprise the second substance and/or further substances (for example in one or more generally non-flowable masses). In a particular embodiment the compartment is comprised in a dropper bottle, and the reservoir is formed by a separate well. The well may be covered, preferably with a removable cover film (preferably without entirely closing the well). Thus a certain protection of the second and further substances may be provided while the well still is accessible from outside. This may be advantageous to provide the package at a relatively high hygiene standard. The dropper bottle may have a pointed outlet cannula capable of piercing the cover film. Thus the cannula may be pushed through the film into the well for delivering liquid from the bottle into well. Thus it may not be necessary to remove the cover foil for joining the first and second substance. The mixture of the first and second substances may therefore also protected by the cover film. The bottle and the well may be provided as a kit comprising at least one bottle and at least one well. Further such a kit may comprise a bottle and a plurality of wells. The plurality of wells may comprise different substances. Thus such a kit may provide for a first substance in a multi-dose container and a plurality of single-use wells. Therefore the dental material may be provided in a single use well which preferably helps maximizing the hygiene, and further part of the dental material may be provided in a multi-dose which preferably helps reducing waste. The advantages of a single-dose and a multi-dose package may thus be combined by the present invention.

In one embodiment the package comprises an applicator. The applicator preferably has a handle end and an applier end. The handle end preferably allows the applicator to be grasped and held by a user, and the applier end preferably allows the dental material (or individual substances of the dental material) to absorb for application at a desired place. The applicator is preferably disposed with its applier end within the reservoir. For example the applicator may be received with its applier end in the opening of the open reservoir. Thus the applier end may be protected from the environment, for example during storage and/or handling of the device.

In another aspect the invention relates to a method of manufacturing a package for a dental material. The method comprises the steps of:
providing the package comprising a compartment for holding a first substance of the dental material;
forming at least part of an open reservoir by a wall of the package for accommodating a second substance of the dental material;
providing a first and a second substance of a dental material; and
retaining the second substance on a surface of the reservoir wall.

The step of providing the package further preferably comprises the step of providing the first substance in the compartment.

In one embodiment the second substance is retained on the reservoir by coating a flowable mass containing the second substance, and causing the flowable mass to harden.

In a further embodiment the method comprises the steps of providing a liquid comprising a film former and at least the second substance to form a coating composition, applying the coating composition to the reservoir wall, and removing at least part of the liquid from the coating composition.

In a further embodiment the method comprises the step of drying the coating composition. Drying may be achieved by applying heat to the coating composition.

In one embodiment the method further comprises the steps of providing a first layer of the package, deep-drawing the first layer to form first and second bulges, providing the first substance in the first bulge, providing the coating composition in the second bulge, and sealing a second layer of the package to the first layer such that the compartment is formed between the first and second layers. Further the method may comprise the step of inserting an applicator in the package or attaching the applicator to the package.

BRIEF DESCRIPTION OF THE FIGURES

FIG. 8 is a cross-sectional view of the package according to an embodiment of the invention;

FIGS. 9a-9c are schematic views illustrating a method of manufacturing of the package according to an embodiment of the invention;

DETAILED DESCRIPTION OF THE INVENTION

Figure 1:
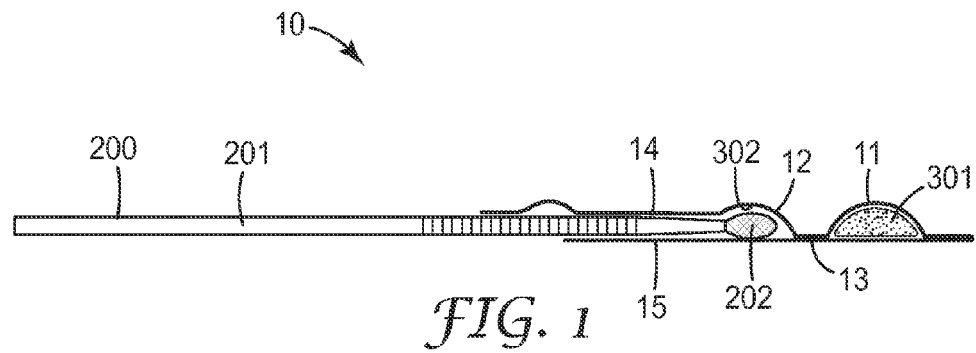
FIG. 1 is a cross-sectional view of a package according to an embodiment of the invention.

FIG. 1 shows a package 10 for a dental material. The package 10 comprises a compartment 11 which encapsulates a preferably liquid first substance 301. Further the package 10 comprises an open reservoir 12. An applicator 200 having a handle end 201 and an applier end 202 is placed with the applier end 202 within the reservoir 12. The applicator 200 in the example is an applicator brush which has a plurality of bristles at the applier end 202. The bristles allow for taking up a portion of the dental material (preferably prepared in the open reservoir) and for applying the material for example to a patient's tooth during a dental treatment. The skilled person will recognize alternative applicators like for example applicators having a sponge or any other suitable structure for taking up a liquid which then can be applied to a desired location, for example in a patient's mouth.

The package 10 further comprises an openable seal 13 which temporarily seals a passage between the compartment 11 and the reservoir 12. The package 10 is adapted such that the openable seal 13 opens in response of a certain minimum pressure inside the compartment 11. Such pressure may be caused by compressing the compartment 11, for example by manually compressing the compartment 11. Thereby the first substance 301 is preferably pressurized and the openable seal, exposed to the pressure, preferably breaks as soon as the pressure exceeds a certain minimum magnitude. In the example the package 10 comprises a first sheet-like layer 14 and a second sheet-like layer 15 which are interconnected with each other to form the compartment 11 and the seal 13. In the area of the seal 13 the interconnection between the layers 14, 15 is non-permanent so that the layers can separate if urged away from one another. Thus by compressing the compartment 11 the first substance 301 may be urged between the layers 14, 15 in the area of the seal so that the seal opens. The skilled person will recognize other packages having different openable seals, like for example a membrane that ruptures due to pressure or a valve which opens pressure controlled, or a seal formed by a valve which can be opened by a user.

The interconnection between the layers 14, 15 in the example entirely surrounds the compartment 11 (in a plane generally transverse to the plane of the view, thus not visible in this view). Thus the layers 14, 15 form the compartment 11 so that the inside of the compartment 11 is entirely sealed relative to the outside. Therefore the first substance 301 may be hermetically sealed within the compartment 11. The package may thus allow storing of the substance over a relatively long time period, for example over several months or years. Preferably the interconnection that surrounds the compartment is permanent over a portion of its circumference and non-permanent over the remaining portion, with the remaining portion forming the openable seal 13. Therefore when the compartment is compressed the non-permanent interconnection is forced open, but not the permanent interconnection.

Such different interconnections may be provided by different bond strengths of the layers in the area of the interconnection. The layers may for example be interconnected by heat sealing, and different bond strengths may be achieved by using different temperatures and/or different sealing durations.

The openable seal 13 preferably extends between the compartment 11 and the reservoir 12. Therefore in an open stage of the seal a passage through the interconnection may be formed which establishes a fluid communication between the compartment 11 and the reservoir 12.

In the example the first layer 14 comprises bulges in the area of the compartment 11 and the reservoir 12. The bulges may be provided in the first layer 14 and/or the second layer 15 to provide a predetermined space for a substance to be received in the compartment and/or the reservoir.

The reservoir 12 in the example is formed between the first layer 14 and the second layer 15. The layers 14, 15 around the reservoir 13 are interconnected, for example permanently interconnected, with each other, and the interconnection is interrupted to form an opening of the reservoir 13.

The reservoir 12 comprises a second substance 302 which is retained (for example by a film former) at a surface of one or both layers 14, 15 (not illustrated in detail). The second substance 302 may be generally non-flowable or non-liquid.

The compartment 11 may be compressed, for example by a user, for activating the package 10 for use. Thereby the seal 13 may be caused to open. Upon further compressing the compartment 11 the substance 301 may be at least partially transferred from the compartment 11 to the reservoir 12, where the (preferably liquid) first substance 301 and the second substance 302 preferably get into contact with one another. The first substance 301 and the second substance 302 may be adapted to at least partially automatically mix with one another, for example due to the second substance dissolving in the first substance. Further the applicator 200 may be used to mix the first and second substances 301, 302 with one another. The mixture of the first and second substances 301, 302 preferably forms the dental material which may be used in a dental treatment.

Figure 2:
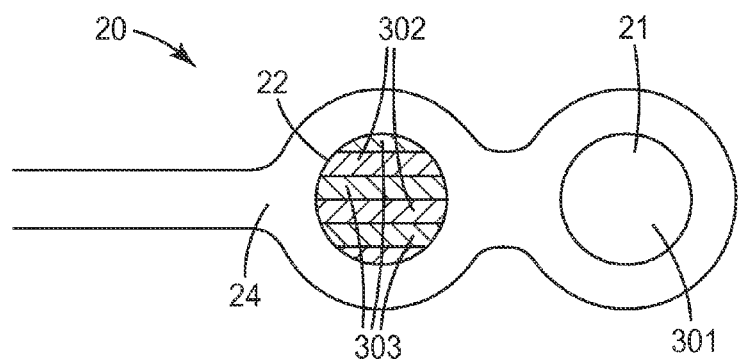
FIG. 2 is a top view on a layer of the package according to an embodiment of the invention.

FIG. 2 is a view inside a package 20 onto a layer 24. The package 20 has a compartment 21 (the inside view provides only a view of part of the compartment) in which a first substance 301 may be stored. Further the package comprises a reservoir 22 formed by at least the layer 24, which accommodates a second substance 302 and a third substance 303. In the example the second and third substances 302, 303 are provided separate from each other on the layer 24. The skilled person will recognize that the package may have a further layer (not shown) which overlaps or covers the reservoir 22 at least partially. Accordingly the first and second substances may be provided on both layers, or only on anyone of the two layers.

In the example the first and second substances are coated alternately side by side and adjacent one another. Such a coating may comprise the first and second substances 302, 303 together with a film former which retains the first and second substances 302, 303 on the layer 24. Because of the mixed prearrangement of the second and third substances in the package a relatively rapid mixing of the second and third substances with the first substance may be achieved.

Figure 3:
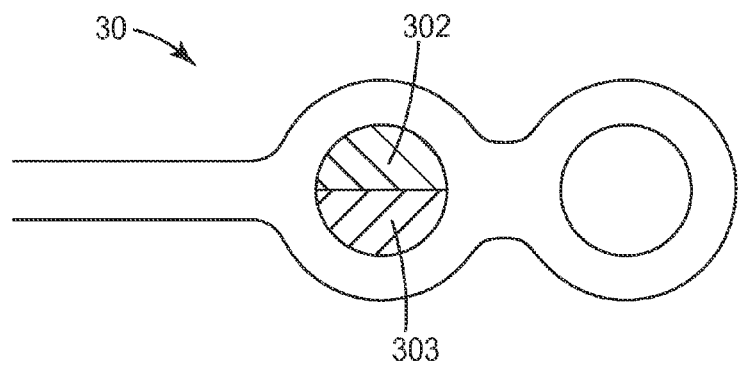
FIG. 3 is a top view on a layer of the package according to a further embodiment of the invention.

FIG. 3 shows a package 30 having a similar coating of the second and third substances 302, 303. In this example the first and second substances 302, 303 are coated in only two adjacent areas. This arrangement may be advantageous in the manufacturing of the package because the pattern is relatively simple and thus relatively easy to apply of a layer of the package. The skilled person will be able to come up with many different patterns for accommodating the second, third and optionally further substances.

Figure 4:
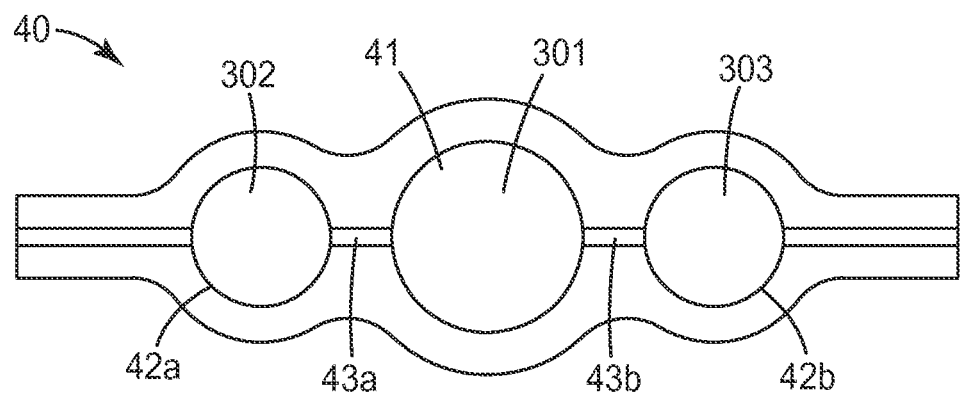
FIG. 4 is a top view on a layer of the package according to another embodiment of the invention.

FIG. 4 shows a package 40 having a compartment 41 in which a first substance 301 may be stored. Further the package 40 has a first reservoir 42a and a second reservoir 42b which accommodate a second substance 302 and a third substance 303, respectively. The second and third substances 302, 303 may be coated at one or two sheet-like layers which form the package as described above. Thus the package 40 comprises two reservoirs 42a, 42b separate from one another. The compartment 41 is separated from the first reservoir 42a by a first openable seal 43a, and separated from the second reservoir 42b by a second openable seal 43b. In the example the compartment 41 is arranged between the reservoirs 42a, 42b. Therefore the package may be activated for use by squeezing the substance toward the first reservoir 42a by compressing the compartment 41 starting at an area adjacent the second seal 43b and successively displacing the compression toward the first seal 43a. Further the package may be activated for use by squeezing the substance toward the second reservoir 42b by compressing the compartment 41 starting at an area adjacent the first seal 43a and successively displacing the compression toward the second seal 43b. Therefore the package may be adapted to provide two different dental materials having a different composition. For example the package may provide a dental material comprising the first and second substances 301, 302 and a dental material comprising the first and third substances 301, 303. The dental material may for example be hardenable and the second and third substances may provide the material with different hardening times. Further the second and third substances may provide the dental material with different color shadings. The skilled person will recognize further applications.

Figure 5:
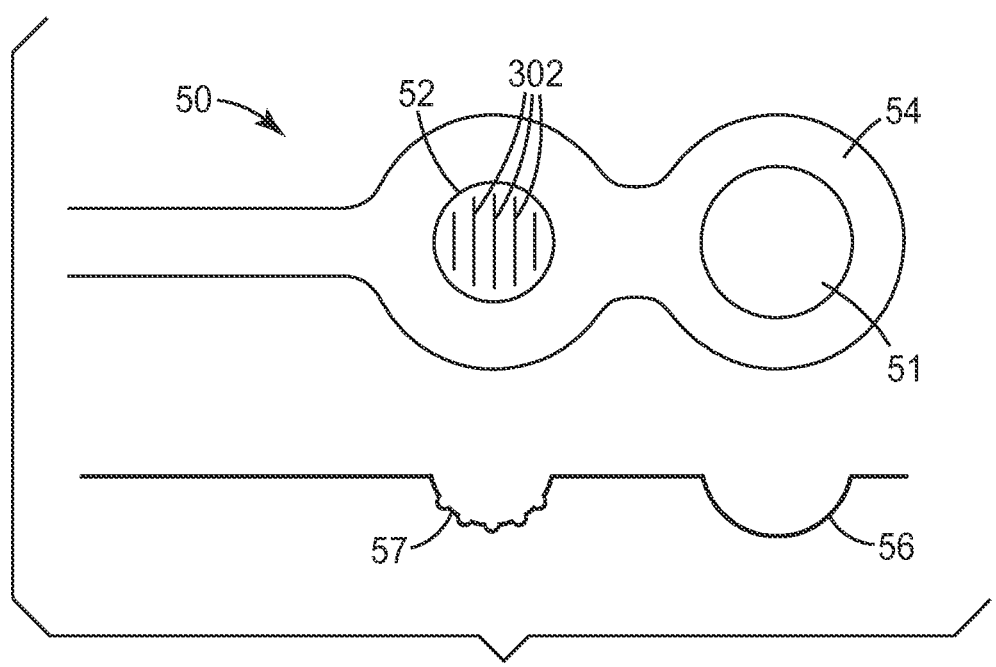
FIG. 5 is a top view on a package layer and a corresponding side view of the package according to an embodiment of the invention.

FIG. 5 shows a layer 54 of a package 50. The layer 54 comprises a compartment bulge 56 forming part of a compartment 51 and a reservoir bulge 57 forming at least part of a reservoir 52. The reservoir bulge 57 comprises a plurality of cavities which in the example are generally bar-shaped. The second substance 302 is preferably provided in the cavities and in more particular in the cavities only. Thus the second substance may be prevented from getting into contact with an applicator which may be inserted in the reservoir (as illustrated in FIG. 1) when the package is still inactivated.

Figure 6:
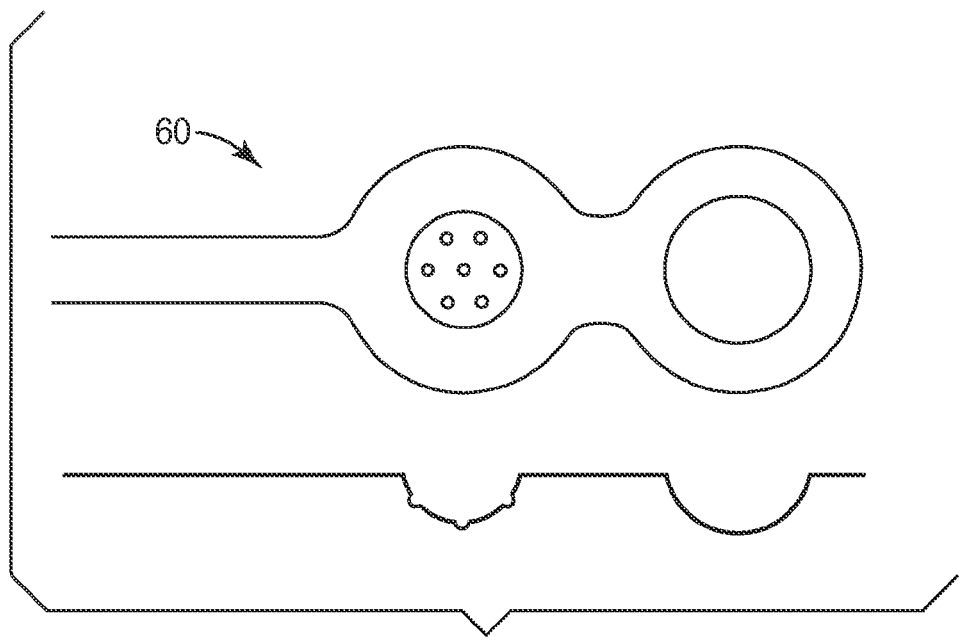
FIG. 6 is a top view on a package layer and a corresponding side view of the package according to a further embodiment of the invention.

FIG. 6 illustrates an embodiment of a package 60 which is similar to the package 50 shown in FIG. 5, but having generally spherical cavities.

Figure 7:
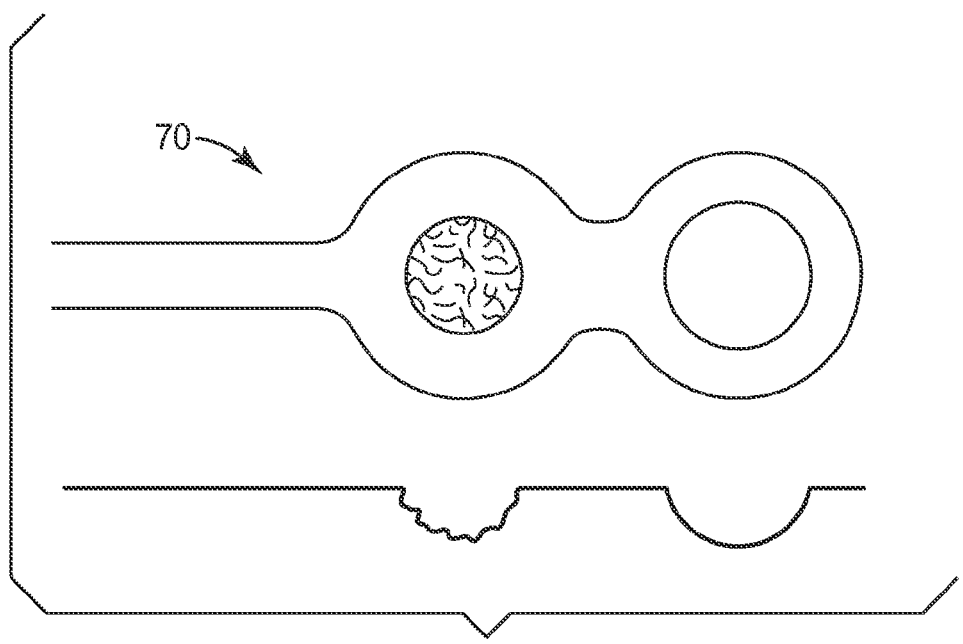
FIG. 7 is a top view on a package layer and a corresponding side view of the package according to still another embodiment of the invention.

FIG. 7 shows an embodiment of a package 70 which is similar to the packages 50 and 60 shown in FIGS. 5 and 6, but with the cavities formed by valleys of a rough surface.

The skilled person will recognize other shapes as well as a combination of different shapes, like for example a combination of bar-shaped cavities, spherical cavities and a rough surface.

The bulges as well as the rough surface may be provided in the layer of the package by embossing. The embossing may be performed in a subsequent step of deep drawing the reservoir bulge, for example. Further embossing may be performed along with deep drawing the reservoir bulge, for example by use of a deep drawing stamp having a shape which also comprises a negative shape of the cavities to be embossed.

FIG. 8 shows a package 80 having a compartment 81 which contains a first substance 301. The package 80 further has an open reservoir 82 which accommodates a second substance 302. The package comprises a first layer 84 which has a compartment bulge 86 and a reservoir bulge 87. The first layer 84 is interconnected with a second layer 85 to form the compartment 81. Further the reservoir 82 is mainly formed by the first layer 84, but with a portion of the second layer 85 overlapping the opening of the reservoir 82. In the example the second substance 302 is retained at a surface of the first layer 84 within the reservoir. In particular the second substance may be retained between the first and second layers 84, 85 within the open reservoir 82.

Upon activation of the package 80 an openable seal 83 separating the compartment and the reservoir 82 from each other preferably is opened due to pressurizing the compartment 81. The first substance 301 may then be squeezed toward the reservoir 82. The package 80 is preferably adapted such that the first substance 301 is guided between the first layer 84 in the area of the reservoir 82 and the overlap of the second layer 85 over the reservoir 82. Therefore the first substance 301 preferably entrains the second substance 302 as it flows from the compartment to the reservoir between the first and second layers 84, 85. The inclusion of the second substance 302 between the overlapping portion of the second layer 85 and the first layer 84 in the reservoir 82 preferably prevents an applicator 200 from getting into contact with the second substance during storage of the still inactivated package 80. Further the passage formed between the first and second layers 84, 85 in the reservoir 82 preferably helps to provide an intense contact between the first and second substances 301, 302 upon activation of the package. Therefore a relatively reproducible mixing ratio of the first and second substances 301, 302 relative to each other and a relative homogeneous mixture from the first and second substances 301, 302 may be achieved by use of the package.

FIGS. 9a-9c illustrate a process of manufacturing a package according to the invention. FIG. 9a shows a first sheet-like layer 94. The first layer 94 may for example be formed by a multi-layer foil comprising an aluminum layer and a plastic layer attached on at least one of the major surfaces of the aluminum layer. The plastic layer is preferably provided to prevent the aluminum layer from getting into direct contact with a substance to be enclosed in the finished package. Further the plastic layer is preferably adapted to allow an interconnection with a second similar layer, for example by heat sealing which causes the plastic layers to merge under heat and pressure. A preferred configuration of the first layer comprises an aluminum layer having a thickness of about 90 μm, a first plastic layer on one side of the aluminum layer having a thickness of about 20 μm and a second plastic layer having a thickness of about 50 μm. Additional adhesive layers may be provided between the aluminum and plastic layers so that the overall thickness of the first layer.

FIG. 9b shows the first layer 94 with a compartment bulge 96 and a reservoir bulge 97. In the example the bulges are formed into the first layer 94 by deep drawing. Thereby a generally spherically shaped stamp is used for each bulge to locally deform the first layer. The stamp may be controlled to provide differently dimensioned deformations for providing different capacities of the compartment and the reservoir. For example a deeper deformation typically provides a higher capacity than a less deep deformation.

At the stage shown a first substance 301 may be filled in the compartment bulge 96, and a second substance 302 may be applied in the reservoir bulge 97. For example the second substance may be dispensed, sprayed or printed as described in more detail further below.

FIG. 9c shows the first layer 94 and a second layer 95 covering the first layer 94. The second layer 95 may be obtained from folding the first layer 94 and thus may form one integrally formed piece with the first layer 94. Further the second layer 95 may be a separate layer from the first layer 94. The configuration of the second layer 95 may be generally similar to the configuration of the first layer 94. The first and/or the second layer(s) are preferably provided on a reel holding a sufficient amount of the layer(s) for manufacturing a plurality of packages, for example a couple of hundred packages.

The first and the second layers 94, 95 are preferably interconnected with one another in a permanent interconnection area 98 and a non-permanent interconnection area 99. The non-permanent interconnection area 99 also corresponds to an openable seal 93. The interconnected layers 94, 95 form a compartment 91 which encloses the first substance 301, and further form an open reservoir 92 accommodating the second substance 302.

The non-permanent interconnection area 99 in the example is shaped such that it extends between the compartment 91 and the reservoir 92 and is restrained by the permanent interconnection otherwise. Therefore the openable seal 93 provided by the non-permanent interconnection area 99 is adapted to establish a fluid communication between the compartment 91 and the reservoir 92.

Figure 10:
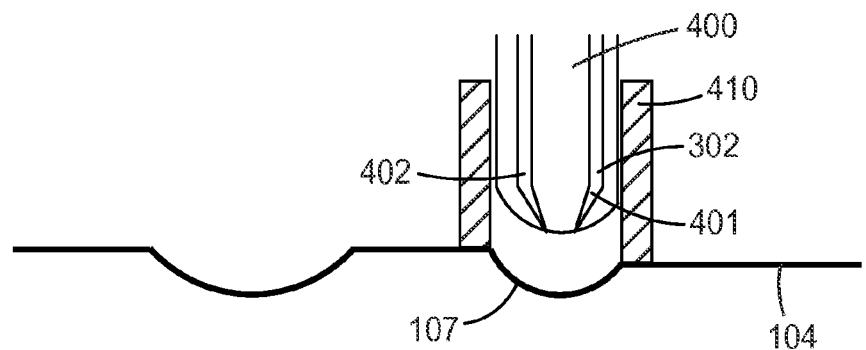
FIG. 10 is a cross-sectional view of a package and a manufacturing tool according to embodiments of the invention.

FIG. 10 illustrates an exemplary method of applying the second substance 302 on a surface of a layer 104 by spraying or printing. A deep drawing stamp 400 is provided which comprises a first nozzle 401 and a second nozzle 402. The deep drawing stamp 400 may be used to provide a reservoir bulge 107 in the layer 104. Through the first nozzle 401 the second substance 302 may be provided. The second substance 302 may be provided in a liquid coating composition which is sprayed through the first nozzle 401.

Accordingly the first nozzle 401 may have an outlet which is adapted to spray the coating composition. A downholder 410 may be provided for sealing off an area to be sprayed from adjacent areas on the layer 104. Further the area to be sprayed may be corona treated prior to spraying the second substance 302 on the layer 104. Therefore the second nozzle 402 may be used to supply ionized air onto the surface of the first layer 104, for example.

In another example (not illustrated) the second substance 302 may be applied by ink jet printing. Accordingly the first nozzle 401 may comprise an ink jet nozzle for printing the second substance 302 provided in the coating composition.

The sprayed or printed coating composition may be exposed to a hardening process such that the coating composition is caused to harden. For example at least part of the liquid may be removed by drying the coating composition so that the remaining coating composition adheres at the first layer 104. The coating composition may further comprise a binder or film former which solidifies as the coating composition is hardened (for example dried).

Other printing methods may be used such as tampon printing, screen printing, for example, or any other suitable printing method.

In a further example the second substance 302 may be pre-printed on a generally flat layer prior to the deep drawing (for example by the foil manufacturer). In the example the second substance 302 may be provided on partial areas of the layer only, for example on areas which are subsequently deep drawn to form a reservoir bulge. Further the second substance may be provided on larger areas of the layer. This may facilitate coating of the second substance, and may make positioning of the coating relative to the deep drawing unnecessary.

Figure 11A:
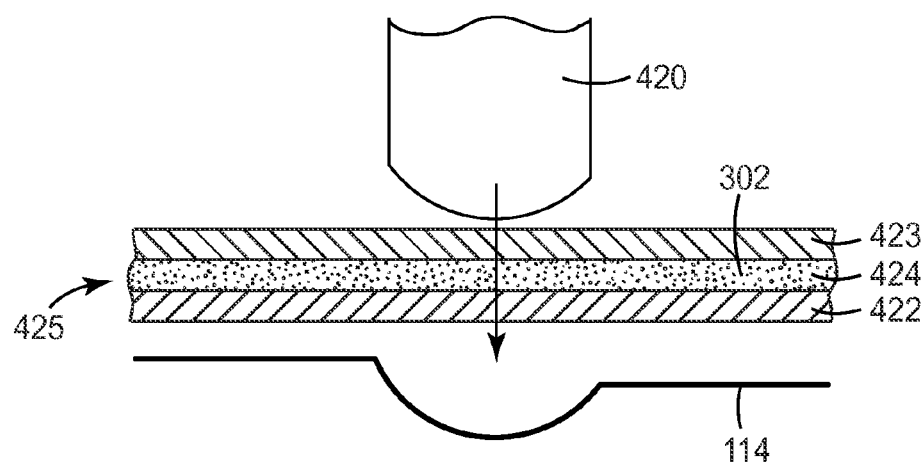
FIGS. 11a, 11b illustrate a method of applying a substance to a package according to an embodiment of the invention.
Figure 11B:
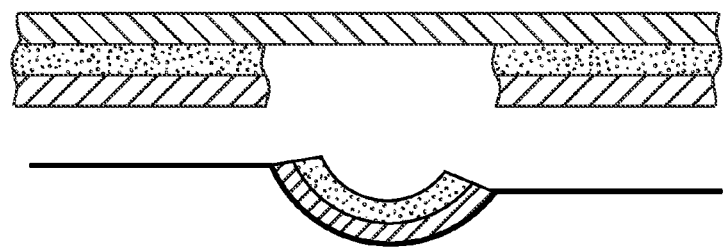

FIGS. 11*a*, 11*b* illustrate a transfer printing method for providing a second substance 302 on a layer 114. A transfer tape 425 may be provided which has a carrier 423. On the carrier 423 the second substance 302 may be provided in a generally non-flowable coating composition 424. The transfer tape 425 may further comprise an adhesive layer 422 provided on the coating composition 424. The bond strength between the carrier 423 and the coating layer 424 may be lower than the bond strength between the coating layer 424 and the adhesive layer 422. This may be achieved by selecting the materials of the carrier 423, the coating layer 424, and the adhesive layer 422 such that the bond strengths are provided by properties of the materials in combination. Further a separating layer (not shown), such a wax layer, for example may be used between the carrier 423 and the coating layer 424 which is adapted to split easily as it is exposed to a pulling force.

A stamp 420 may be used to press a partial area of the transfer tape with the adhesive layer 422 leading toward a surface of the layer 114. The stamp may be heated, for example in case a separating layer is used. Upon retracting the stamp and the tape from the layer 114 the adhesive layer preferably retains the coating composition, and the coating composition preferably loosens from the carrier. Thus in the partial area pressed by the stamp the adhesive layer and the coating layer separate from the carrier and further separate from areas outside the partial area pressed. In other words a print having substantially the shape of the stamp and comprising the second substance 302 may be transferred from the transfer tape onto the layer 114. The transfer tape may be provided on a reel holding sufficient tape for a plurality of prints.

In another example an adhesive layer may not be present so that the coating layer can be directly brought in contact with the layer 114 during the printing. In this case the coating layer may comprise a binder or film former which captures the second substance and which is further adapted to bond with the layer 114, for example when heat sealed to the layer 114.

The skilled person will recognize that the methods of applying the second substance to the layer illustrated in the example may further be used to apply the second substance to other layers. In particular the second substance may be applied to the first and second layers of a package according to the invention, or on only one of the first and second layers.

Further the skilled person will recognize that the second substance in particular embodiments may correspond to the coating composition so that the coating composition only comprises the second substance, whereas in other examples the second substance may together with further components, like for example a binder or film former, form the coating composition.

The skilled person will further recognize that a third substance or further substances may be applied to the package in the same or similar manner as it is describe for the second substance herein.

The invention claimed is:

1. A package for a dental material, comprising a compartment for holding a first substance of the dental material and an open reservoir at least partially formed by a wall of the package, wherein the compartment and the reservoir are connectable for fluid communication, wherein a second substance of the dental material is retained at a surface of a wall of the reservoir by a film former comprised in the second substance, and wherein the film former forms a solid film.

2. The package of claim 1, wherein the compartment is formed between interconnected sheet layers of the package, and wherein the reservoir is formed by at least one of the sheet layers.

3. The package of claim 2, wherein one of the sheet layers comprises a compartment bulge forming part of the compartment and a reservoir bulge forming at least part of the reservoir.

4. The package of claim 1, further comprising an openable seal separating the reservoir and the compartment from each other, wherein the seal is formed by an area in which the layers are interconnected, the interconnection in this area being non-permanent, such that the seal is adapted to separate upon forcing the first substance between the layers.

5. The package of claim 1, in which the reservoir comprises a cavity which is open toward the reservoir, and wherein the second substance is at least partially accommodated in the cavity.

6. The package of claim 5, comprising a plurality of similar or differently shaped cavities.

7. The package of claim 5, wherein the cavities are formed by a rough surface having a surface roughness Ra of between about 10 µm and about 500 µm according to DIN EN ISO 4287 or 4288 respectively.

8. The package of claim 5, wherein the cavity is formed by a bulge in a wall of the reservoir.

9. The package of claim 1, in which the reservoir accommodates an additional third substance.

10. The package of claim 9, in which the reservoir comprises a coating in which at least a portion of at least one of the second and third substances is accommodated.

11. The package of claim 9, in which the coating comprises a first coating area in which at least a portion of the second substance is accommodated, and a second coating area in which at least a portion of the third substance is accommodated.

12. The package of claim 1, further comprising a second reservoir in which a third substance is accommodated, wherein the package comprises a first seal separating the first reservoir and the compartment from one another, and a second seal separating the second reservoir and the compartment from one another.

13. The package of claim 1, comprising an applicator, the applicator having a handle end and an applier end, wherein the applicator is disposed with its applier end within the reservoir.

14. The package of claim 1, wherein the reservoir is open and wherein the second substance is retained at a surface of a wall of the reservoir.

15. The package of claim 1, further comprising a first layer having a compartment bulge and a reservoir bulge, and a second layer interconnected with the first layer to form the compartment, wherein a portion of the second layer overlaps an opening of the reservoir.

16. A method of manufacturing a package for a dental material, comprising:
 providing the package comprising a compartment for holding a first substance of the dental material;
 forming at least part of an open reservoir by a wall of the package for accommodating a second substance of the dental material;
 providing the first substance and the second substance of the dental material; and
 retaining the second substance on a surface of a wall of the reservoir, wherein the second substance is retained at a surface of the wall of the reservoir by a film former comprised in the second substance, and wherein the film former forms a solid film.

\* \* \* \* \*